United States Patent [19]

Barth

[11] Patent Number: 4,590,073
[45] Date of Patent: May 20, 1986

[54] 6-SUBSTITUTED PENICILLANIC ACID 1,1-DIOXIDE COMPOUNDS

[75] Inventor: Wayne E. Barth, East Lyme, Conn.

[73] Assignee: Pfizer Inc., New York, N.Y.

[21] Appl. No.: 751,331

[22] Filed: Jul. 2, 1985

Related U.S. Application Data

[63] Continuation-in-part of Ser. No. 663,910, Oct. 22, 1984, abandoned.

[51] Int. Cl.$^4$ .................. C07D 499/00; A61K 31/415
[52] U.S. Cl. .............................. 424/114; 260/245.2 R
[58] Field of Search ................. 260/245.2 R; 514/192; 424/114

[56] References Cited

U.S. PATENT DOCUMENTS 4,234,579 11/1980 Barth .................................. 424/246
4,287,181 9/1981 Kellogg .............................. 424/114
4,452,796 6/1984 Barth .................................. 424/246
4,536,393 8/1985 Barth ............................ 260/245.2 R

FOREIGN PATENT DOCUMENTS 2053220 2/1981 United Kingdom .

Primary Examiner—Nicholas S. Rizzo
Attorney, Agent, or Firm—Charles J. Knuth; Peter C. Richardson; J. Trevor Lumb

[57] ABSTRACT

A series of novel derivatives of penicillanic acid 1,1-dioxide, having a disubstituted methyl group of the formula X—CH—Y at the 6-position, and the pharmaceutically-acceptable salts thereof and the pharmaceutically-acceptable esters thereof readily hydrolyzable in vivo, wherein X is hydroxy, acylated hydroxy or amino and Y is carboxy or esterified carboxy. The compounds of the invention are inhibitors of bacterial beta-lactamases, and they will protect certain beta-lactamase-susceptible beta-lactam antibiotics, e.g. ampicillin, against inactivation by beta-lactamases. Co-administration of a compound of the invention with a beta-lactam antibiotic such as ampicillin to a mammalian subject increases the effectiveness of the beta-lactam antibiotic against infections caused by beta-lactamase-producing bacteria.

23 Claims, No Drawings

6-SUBSTITUTED PENICILLANIC ACID 1,1-DIOXIDE COMPOUNDS

CROSS-REFERENCE TO RELATED APPLICATION

This application is a continuation-in-part of application Ser. No. 663,910, filed Oct. 22, 1984, now abandoned.

BACKGROUND OF THE INVENTION

This invention relates to new chemical compounds. More particularly it relates to new chemical compounds which are of value for use in combination with beta-lactam antibiotics, to increase their effectiveness.

One of the most well-known and widely-used classes of antibacterial agents is the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which degrade the penicillin or cephalosporin, rendering it inactive as an antibacterial agent. However, certain substances will inhibit beta-lactamase enzymes, and when a beta-lactamase inhibitor is used in combination with a beta-lactamase-susceptible beta-lactam antibiotic, the effectiveness of the beta-lactam antibiotic is increased or enhanced. Such an effect is known as synergy. Synergy is deemed to be exhibited by a combination of a beta-lactamase inhibitor and a beta-lactam antibiotic when the antibacterial activity of the combination is significantly greater than the sum of the antibacterial activities of the individual components.

Thus, the present invention provides certain new chemical substances which are potent inhibitors of bacterial beta-lactamases. More specifically, these new chemical substances are derivatives of penicillanic acid 1,1-dioxide having a disubstituted methyl group at the 6-position, and certain salts and esters thereof. Said disubstituted methyl group is of the formula X—CH—Y, where X is hydroxy, acylated hydroxy or amino and Y is a carboxy group or an esterified carboxy group.

Penicillanic acid 1,1-dioxide itself, sulbactam, is a well-known beta-lactamase inhibitor (U.S. Pat. No. 4,234,579), and 6-(hydroxyalkyl) and 6-(aminoalkyl) derivatives thereof are also known to possess beta-lactamase inhibitory properties (U.S. Pat. Nos. 4,287,181 and 4,452,796). Published British patent application No. 2,053,220 refers in a broad and general way to penicillanic acid 1,1-dioxide compounds, allegedly having beta-lactamase inhibiting properties.

SUMMARY OF THE INVENTION

This invention provides novel penicillanic acid 1,1-dioxide compounds selected from the group consisting of

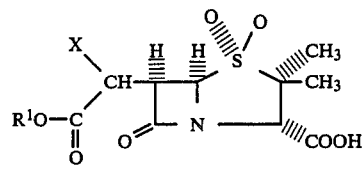

(I)

and

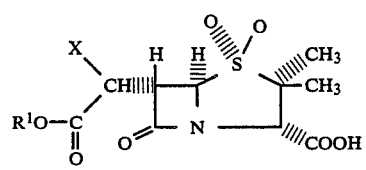

(II)

and the pharmaceutically-acceptable base salts thereof, and the pharmaceutically-acceptable esters thereof readily hydrolyzable in vivo, wherein $R^1$ is selected from the group consisting of hydrogen and alkyl having 1 to 4 carbons; and X is selected from the group consisting of hydroxy, alkanoyloxy having 2 to 5 carbons and amino.

Said compounds of formulae I and II, and said pharmaceutically-acceptable salts and esters thereof, are useful as inhibitors of bacterial beta-lactamases, and they protect beta-lactamase-susceptible beta-lactam antibiotics against degradation by beta-lactamase enzymes. Accordingly, this invention also provides an improved method for the treatment of bacterial infections caused by beta lactamase producing bacteria in mammalian subjects, which comprises using a beta-lactamase inhibitor of this invention in combination with a beta-lactam antibiotic; and also pharmaceutical compositions comprising a beta-lactamase inhibitor of this invention and a pharmaceutically-acceptable carrier or diluent.

A preferred group of compounds of this invention consists of the compounds of formula I, and said pharmaceutically-acceptable salts and esters thereof, wherein $R^1$ is said alkyl. Within this preferred group, a first particularly preferred sub-group consists of those compounds in which $R^1$ is said alkyl and X is hydroxy, and a second particularly preferred sub-group consists of those compounds in which $R^1$ is said alkyl and X is amino.

Especially desirable individual beta-lactamase inhibitors of this invention are: (8R)-6-beta-[(hydroxy)-(methoxycarbonyl)methyl]penicillanic acid 1,1-dioxide and (8S)-6-beta-[(amino)(methoxycarbonyl)methyl]penicillanic acid 1,1-dioxide.

Also included with the scope of this invention are compounds of the formulae

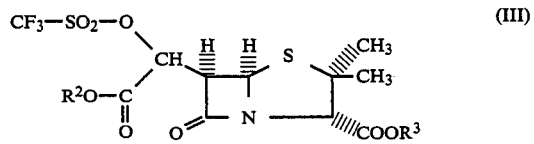

(III)

-continued and

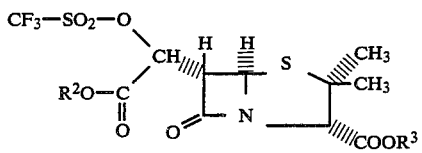

wherein $R^2$ is alkyl having from 1 to 4 carbons or a carboxy protecting group, and $R^3$ is a carboxy protecting group. A particularly useful carboxy protecting group both for $R^2$ and $R^3$ is the benzyl group. These compounds of formulae III and IV are useful as intermediates to the beta-lactamase inhibitors of this invention of formulae I and II, wherein X is amino.

DETAILED DESCRIPTION OF THE INVENTION

The beta-lactamase inhibitors of this invention are the compounds of formulae I and II. In this specification, these compounds and a number of intermediates leading thereto are named as derivatives of penicillanic acid, which is the compound of the following formula:

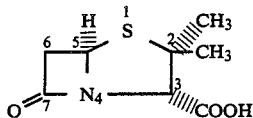

In the formula for penicillanic acid, broken line attachment of a substituent to the bicyclic nucleus indicates that the substituent is below the plane of the bicyclic nucleus. Such a substituent is said to be in the alpha-configuration. Conversely, solid line attachment of a substituent to the bicylic nucleus indicates that the substituent is attached above the plane of the nucleus. This latter configuration is referred to as the beta-configuration. Additionally, many of the penicillanic acid derivatives in this specification have a substituent attached at the C-6 position, and when the substituent is attached through a carbon atom this carbon atom is referred to as the 8-position. Moreover, when the C-8 carbon atom is asymmetrically substituted, the configuration at C-8 is designated as (R) or (S), as defined in the Cahn-Ingold-Prelog rules for designating absolute stereochemistries. Cahn and Ingold, *Journal of the Chemical Society* (London), 612 (1951); Cahn, Ingold and Prelog, *Experientia,* 12, 81 (1956).

As indicated hereinbefore, this invention embraces the pharmaceutically-acceptable esters of the compounds of the formula I and II which are readily hydrolyzable in vivo. These types of esters are now quite conventional for penicillanic acid compounds. In general, they are esters which are readily cleaved under physiological conditions, e.g. after administration of such an ester to a mammalian subject, to liberate the free acid and pharmaceutically-acceptable (i.e. nontoxic) fragments. In many instances, formation of such an ester from a carboxylic acid improves the oral absorption characteristics of the parent acid.

A wide variety of ester-forming radicals which give pharmaceutically-acceptable esters readily hydrolyzable in vivo are now known. For example, see U.S. Pat. No. 4,446,144 and published European patent application No. 13,617. However, in the present instance, particularly useful radicals are 3-phthalidyl, 4-crotonolactonyl, and gamma-butyrolacton-4-yl radicals, and radicals of the formula —CH($R^4$)—O—C(=O)—$R^5$, wherein $R^4$ is hydrogen, methyl or ethyl and $R^5$ is alkyl of 1 to 5 carbons or alkoxy of 1 to 5 carbons. Especially preferred individual esters readily hydrolyzable in vivo of the beta-lactamase inhibitors of formulae I and II are the pivaloyloxymethyl and the 1-(ethoxycarbonyloxy)ethyl esters.

The compounds of formulae I and II, wherein $R^1$ and X are as defined previously can be prepared from the appropriate compound of the formula

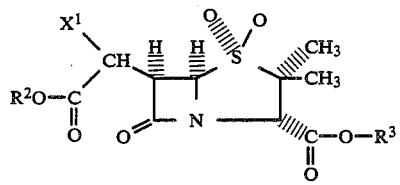

or

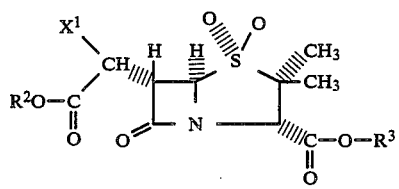

wherein $R^2$ is alkyl having from 1 to 4 carbons or a carboxy protecting group, $R^3$ is a carboxy protecting group, and $X^1$ is selected from the group consisting of hydroxy, alkanoyloxy having 2 to 5 carbons, amino, protected-amino and pro-amino groups. This is achieved as follows:

(a) a compound of formula I or II, wherein $R^1$ is alkyl and X is hydroxy or alkanoyloxy, is prepared from the appropriate compound of formula V or VI, wherein $R^2$ is alkyl and $X^1$ is hydroxy or alkanoyloxy, by removal of the protecting group $R^3$;

(b) a compound of formula I or II, wherein $R^1$ is hydrogen and X is hydroxy or alkanoyloxy, is prepared from the appropriate compound of formula V or VI, wherein $R^2$ is a carboxy protecting group and $X^1$ is hydroxy or alkanoyloxy, by removal of the protecting groups $R^2$ and $R^3$;

(c) a compound of formula I or II, wherein $R^1$ is alkyl and X is amino, is prepared from the appropriate compound of the formula V or VI, wherein $R^2$ is alkyl and $X^1$ is protected-amino or pro-amino, by removal of the protecting group $R^3$ and conversion of $X^1$ into amino; and (d) a compound of formula I or II, wherein $R^1$ is hydrogen and X is amino, is prepared from the appropriate compound of the formula V or VI, wherein $R^2$ is a carboxy protecting group and $X^1$ is protected-amino or proamino, by removal of the protecting groups $R^2$ and $R^3$ and conversion of $X^1$ into amino.

In method (b) above, removal of the protecting groups $R^2$ and $R^3$ can be carried out in either order; in method (c) above, removal of the protecting group and conversion of $X^1$ into amino can be carried out in either order; and in method (d) above, removal of the protecting groups $R^2$ and $R^3$ and conversion of $X^1$ into amino can be carried out in any order.

A variety of protecting groups conventionally used in the penicillin art to protect carboxy groups can be used for $R^2$ and $R^3$. The major requirement for such a group is that it can be removed using conditions under which the beta-lactam ring of the compounds of formula I, II, V and VI is stable, and it permits easy access to the compound of V or VI by the methods described hereinbelow.

When $X^1$ is protected amino, it represents an amino group protected by a protecting group conventionally used in the penicillin art for this purpose. This protecting group must also be removable using conditions under which the beta-lactam ring of a compound of the formula I, II, V and VI is stable.

The term "pro-amino group" refers to a group which is readily converted into an amino group under conditions which are sufficiently mild to avoid decomposition of the starting material of formula V or VI or the product of formula I or II. Such groups have been used previously in the penicillin art to prepare amino-substituted penicillin compound, e.g. ampicillin, amoxicillin, bacampicillin, and the like.

For the purposes of the present invention, it has been found that for preparation of a compound of formula I or II wherein $R^1$ is alkyl, it is convenient to choose a protecting group $R^3$ which is readily removable by catalytic hydrogenation, and, for preparation of a compound wherein $R^1$ is hydrogen, it is convenient to choose a group for $R^2$ which is also removable by catalytic hydrogenation. Also, when it is desired to prepare a compound in which X is amino, it is convenient to choose a protected amino or a pro-amino group which is readily converted into amino by catalytic hydrogenation. In this way, removal of $R^3$ (and $R^2$ if desired) to give a free carboxy group, and conversion of $X^1$ into amino if desired, can be achieved effectively in a single step. Under these circumstances, convenient groups for $R^2$ and $R^3$ are benzyl and 4-nitrobenzyl, especially benzyl; convenient protected-amino groups for $X^1$ are benzyloxycarbonylamino and 4-nitrobenzyloxycarbonylamino, especially benzyloxycarbonylamino; and a convenient pro-amino group for $X^1$ is azido.

Thus, a compound of formula I or II, wherein $R^1$ is hydrogen or alkyl having 1 to 4 carbons and X is hydroxy, alkanoyloxy having 2 to 5 carbons or amino, can be prepared from the corresponding compound of formula V or VI, wherein $R^2$ is said alkyl or benzyl, $R^3$ is benzyl, and $X^1$ is hydroxy, said alkanoyloxy, benzyloxycarbonylamino or azido, by catalytic hydrogenation using conventional methods. One convenient method of carrying out this transformation is to stir or shake a solution of a compound of the formula V or VI, or a mixture thereof, under an atmosphere of hydrogen, or hydrogen mixed with an inert diluent such as nitrogen or argon, in the presence of a hydrogenation catalyst. Suitable solvents for this reaction are those which substantially dissolve the starting compound of the formula V or VI, are sufficiently volatile to be removed by evaporation, and do not themselves suffer hydrogenation. Examples of such solvents include ethers such as diethyl ether, tetrahydrofuran, dioxan, 1,2-dimethoxyethane; low molecular weight esters such as ethyl acetate and butyl acetate; tertiary amides such as N,N-dimethylformamide, N,N-dimethylacetamide and N-methylpyrrolidone; water; and mixtures thereof. Introduction of the hydrogen gas into the reaction medium is usually accomplished by carrying out the reaction in a sealed vessel containing the compound of the formula V or VI, or mixture thereof, the solvent, the catalyst and the hydrogen. The pressure inside the reaction vessel can vary from about 1 to about 100 kg/cm², the preferred range when the atmosphere inside the reaction vessel is substantially pure hydrogen, being from about 2 to about 20 kg/cm². The hydrogenation is generally run at a temperature of from about 0° C. to about 60° C., and preferably from about 25° to about 40° C. Utilizing the preferred temperature and pressure values, hydrogenation generally takes place quite rapidly and it is usually complete within a few hours, e.g. two hours. The catalysts used in this hydrogenation reaction are the type of agents known in the art for this kind of transformation, and typical examples are the noble metals, such as nickel, palladium, platinum and rhodium. The catalyst is usually present in an amount from about 1 to about 20 weight-percent, and preferably from about 5 to about 10 weight-percent, based on the compound of formula V or VI, or mixture thereof. It is often convenient to suspend the catalyst on an inert support. A particularly convenient catalyst is palladium suspended on an inert support such as carbon, e.g. 10% by weight palladium on carbon.

The compounds of formula I and II can be isolated after hydrogenation of a compound of formula V or VI by standard methods. At the end of the reaction, the catalyst is removed by filtration, and then any organic solvents can be removed by evaporation in vacuo and any aqueous solvent by lyophilization. Alternatively, when an aqueous or partially aqueous solvent system has been used for the hydrogenation, a compound of formula I or II, wherein X is hydroxy or alkanoyloxy, can be recovered by removal of the catalyst by filtration, evaporation of any water-miscible, organic solvent in vacuo, and extraction of the product into a volatile, water-immiscible, organic solvent at an acidic pH (e.g. a pH form 1 to 4). Evaporation of the latter solvent then affords the crude product. Still further, when an aqueous or partially aqueous solvent system has been used for the hydrogenation, a compound of formula I or II, wherein X is amino, can be recovered by removal of the catalyst by filtration, evaporation of any organic solvent and adjustment of the pH of the remaining aqueous phase to the isoelectric point of the product. The product is then induced to precipitate by reducing the aqueous phase to small volume, and, if necessary, adding a small amount of a water-miscible, organic solvent. Finally the crude product of formula I, wherein X is amino, is recovered by filtration.

A beta-lactamase inhibitor of the formula I or II can be purified by standard procedures, well-known in the art, such as recrystallization or chromatography, e.g. chromatography on sephadex.

The compounds of formula V, wherein $R^2$ is alkyl having 1 to 4 carbons or benzyl, $R^3$ is benzyl and $X^1$ is hydroxy, alkanoyloxy having 2 to 5 carbons, benzyloxycarbonylamino or azido can be prepared from the corresponding compound of the formula

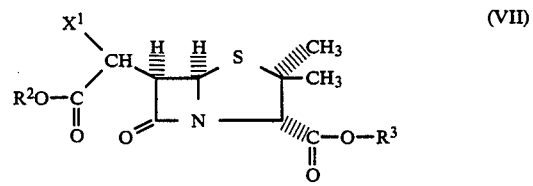

(VII)

This is a classical oxidation reaction of a sulfide to a sulfone, and it can be brought about using a variety of reagents known in the art for carrying out this type of transformation in penicillin compounds. For example, convenient oxidants are organic peroxycarboxylic acids, such as 3-chloroperbenzoic acid. When a compound of formula VII is oxidized to the corresponding compound of formula V using 3-chloroperbenzoic acid, the reaction is usually carried out by treating the compound of the formula VII with from about 2 to about 6 molar equivalents, and preferably about 3 molar equivalents of the oxidant, in a reaction-inert organic solvent. Typical solvents are chlorinated hydrocarbons, such as dichloromethane, chloroform and 1,2-dichloroethane; low-molecular weight esters, such as ethyl acetate and butyl acetate; and ethers, such as diethyl ether, tetrahydrofuran and 1,2-dimethoxyethane. The reaction is normally carried out at a temperature of from about $-30°$ to about 50° C., and preferably from about 15° to about 30° C. At about 25° C., reaction times of about 4 to about 24 hours are commonly used. When a water-immiscible, organic solvent has been used, the product can be isolated by washing the reaction mixture with sodium bisulfite solution followed by sodium bicarbonate solution (to remove the 3-chlorobenzoic acid by-product), and then evaporating the organic solvent in vacuo. When a water-miscible, organic solvent has been used for the oxidation, the product can be isolated by removing the reaction solvent in vacuo, decomposing excess peracid with sodium bisulfite and then partitioning the residue between sodium bicarbonate solution and a volatile, water-immiscible, organic solvent. Separation of the two layers, and evaporation of the organic layer, then affords the crude product.

A compound of formula VI, wherein $R^2$ is alkyl having 1 to 4 carbons or benzyl, $R^3$ is benzyl and $X^1$ is hydroxy, alkanoyloxy having 2 to 5 carbons, benzyloxycarbonylamino or azido, can be prepared form the corresponding compound of formula V, i.e. from its C-6 epimer. This epimerization reaction is carried out by treatment of said compound of formula V with a basic catalyst, and a convenient catalyst for this purpose is 1,5-diazabicyclo[4.3.0]non-5-ene, which is often referred to in the art as "DBN." In a typical procedure, a compound of the formula V is contacted with an equimolar amount, or slightly less than an equimolar amount, of DBN in an inert solvent, such as dichloromethane or chloroform, at around 25° C. Epimerization takes place quite rapidly, and it is normally essentially complete within a few minutes, e.g. 2 to 5 minutes. The basic catalyst is then neutralized, e.g. with a small excess of glacial acetic acid, thereby quenching the reaction, and the product is isolated by standard methods. For example, the dichloromethane or chloroform solvent is washed with water to remove the basic catalyst (as its salt), and then evaporation of the dichloromethane or chloroform affords the desired 6-alpha-epimer of formula VI.

The compounds of the formula VII, wherein $R^2$ is alkyl having 1 to 4 carbons or benzyl, $R^3$ is benzyl and $X^1$ is hydroxy or benzyloxycarbonylamino can be prepared via a two-step procedure from benzyl 6,6-dibromopenicillanate, the compound of the formula VIII

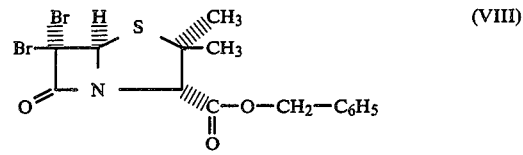

In the first step, the dibromo compound of the formula VIII is reacted, at low temperature (e.g $-78°$ C.), in an ether solvent (e.g. diethyl ether or tetrahydrofuran), with one molar equivalent of methylmagnesium bromide followed by one molar equivalent of a glyoxylate ester of the formula IX or an ester of the formula X:

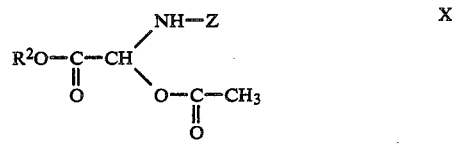

wherein $R^2$ is alkyl having 1 to 4 carbons or benzyl and Z is the benzyloxycarbonyl group. After appropriate work-up, this affords a compound of the formula XI:

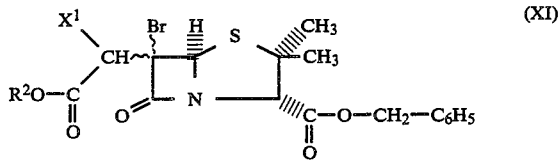

In practice, reaction of the dibromo compound of formula VIII with methylmagnesium bromide followed by a compound of the formula IX or X leads to the product XI as a mixture of isomers. While the full stereochemical details of this reaction sequence have not been worked out, it appears that both 6-alpha-bromo and 6-beta-bromo products are formed, and both (8R)-products and (8S)-products are formed. Partial separation of the mixture has been achieved by chromatography, but all possible diastereomers have not been isolated.

In the second step of the aforesaid two-step procedure, a compound of the formula XI is reduced with a trialkyltin hydride, e.g. tri-n-butyltin hydride, according to known procedures. See further, U.S. Pat. No. 4,397,783 and published European patent application No. 13,617. In this reduction, the stereochemistry at the 6-position of the starting compound of formula XI is not critical. Thus, irrespective of the stereochemistry of the starting compound of formula XI, the reduction leads predominantly in each case to a compound of formula VII (i.e. a compound in which the $R^2O-C(=O)-CH-X^1$ substituent is in the beta-configuration).

A compound of the formula VII, wherein $R^2$ is alkyl having 1 to 4 carbons or benzyl, $R^3$ is benzyl and $X^1$ is alkanoyloxy having 2 to 5 carbons, can be obtained from the corresponding compound in which $X^1$ is hydroxy by acylation. This is carried out by standard procedures. In a typical procedure, the alcohol of formula VII is treated with a small excess of an acid anhydride of the formula (R$^6$O—CO)$_2$O, where R$^6$ is alkyl having 1 to 4 carbons, in the presence of a basic catalyst (e.g. pyridine), in a reaction-inert solvent (e.g. tetrahydrofuran), at about 25° C. The reaction proceeds quite quickly, and it is complete within a few hours. The solvent is removed by evaporation in vacuo, and the residue is partitioned between ethyl acetate and sodium bicarbonate solution. Separation of the phases, and evaporation of the dried organic phase affords the desired compound of formula VII, wherein X$^1$ is alkanoyloxy.

A compound of the formula VII, wherein R$^2$ is alkyl having from 1 to 4 carbons or benzyl, R$^3$ is benzyl and X$^1$ is azido, can be prepared from the corresponding compound of the formula

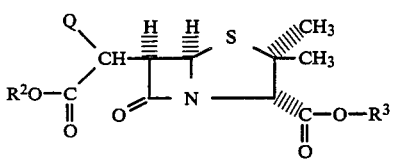

wherein Q is a good leaving group, by reaction with a source of azide ion. A variety of groups can be used for Q; however, a particularly convenient group in the present instance is the trifluoromethanesulfonyloxy group. A convenient source of azide ion is tetra-n-butylammonium azide. Thus, in a typical procedure, a solution of a compound of formula XII, wherein Q is trifluoromethanesulfonyloxy, is contacted with an excess of tetra-n-butylammonium azide in an inert solvent such as dichloromethane at a temperature in the range from about −15° to about 0° C. The product can be isolated simply by removal of the solvent by evaporation, and the product is usually purified by column chromatography, e.g. on silica gel.

A compound of the formula XII, wherein R$^2$ is alkyl having 1 to 4 carbons or benzyl, R$^3$ is benzyl and Q is trifluoromethylsulfonyloxy, can be prepared from the corresponding compound of formula VII, wherein X$^1$ is hydroxy. This is achieved by acylation using trifluoromethanesulfonic anhydride. The method described earlier for the acylation of a compound of formula VII, wherein X$^1$ is hydroxy, using an anhydride of the formula (R$^6$O—CO)$_2$O can be used, except that lower temperatures, e.g. temperatures in the range from −20° to 0° C., are preferred. The compound of formula XII, wherein Q is trifluoromethylsulfonyloxy, can be isolated by standard methods. However, it is convenient to use this compound in solution, without isolation, for reaction with azide ion.

A compound of the formula VI, wherein R$^2$ is alkyl having from 1 to 4 carbons or benzyl, R$^3$ is benzyl and X$^1$ is azido, can be prepared from a compound of the formula VII, wherein R$^2$ is alkyl having 1 to 4 carbons or benzyl, R$^3$ is benzyl and X$^1$ is hydroxy, by a variation of the above-mentioned method. This is achieved by the following sequence:

1. epimerization to give the corresponding 6-alpha-epimer of the formula

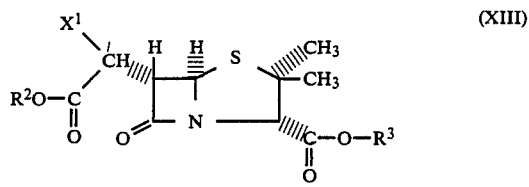

wherein R$^2$ is alkyl having from 1 to 4 carbons or benzyl, R$^3$ is benzyl and X$^1$ is hydroxy;

2. acylation with trifluoromethanesulfonic anhydride to give the corresponding compound of the formula

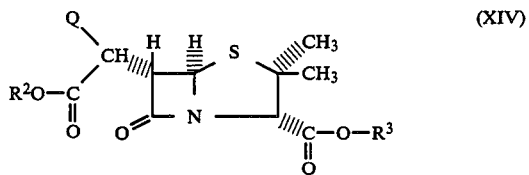

wherein R$^2$ is alkyl having from 1 to 4 carbons or benzyl, R$^3$ is benzyl and Q is trifluoromethylsulfonyloxy;

3. displacement of the group Q by azide ion to give the corresponding azido compound of the formula

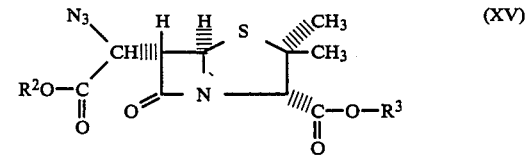

wherein R$^2$ is alkyl having 1 to 4 carbons or benzyl and R$^3$ is benzyl; and 4. oxidation to give the compound of formula VI, wherein R$^2$ is alkyl having 1 to 4 carbons or benzyl, R$^3$ is benzyl and X$^1$ is azido.

In the above sequence, step 1 can be carried out using DBN by the method described earlier for epimerization of a compound of formula V, but using somewhat longer reaction times; step 2 can be carried out by the method described earlier for acylation of a compound of formula VII, wherein X$^1$ is hydroxy; step 3 can be carried out using tetra-n-butylammonium azide by the method described earlier for a compound of formula XII, wherein Q is trifluoromethylsulfonyloxy; and step 4 can be carried out using 3-chloroperbenzoic acid by the method described earlier for a compound of formula VII.

The carbon atom attached to the 6-position of the compounds of formulae I to VII and XI to XV is asymmetrically-substituted, and therefore these compounds can exist in one of two forms, the (8R)-configuration or the (8S)-configuration, or as a mixture of these forms. However, during the transformations V or VI to I or II, V to VI, VII to V, or XV to VI, or during acylation of a compound of formula VII or XIII, wherein X$^1$ is hydroxy, the configuration at C-8 is largely unchanged. On the other hand, reaction of a compound of the formula XII or XIV, wherein Q is trifluoromethylsulfonyloxy, with azide ion results in inversion of the configuration at C-8, i.e. the incoming azide group assumes a position opposite from that previously occupied by the trifluoromethylsulfonyloxy group.

Benzyl 6,6-dibromopenicillanate, the compound of formula VIII, can be prepared by the method of DiNinno et al., *Journal of Organic Chemistry*, 42, 2960 (1977).

The glyoxylate esters of the formula IX can be prepared by known methods, or methods analogous to known methods. See further: Hook, *Synthetic Communications*, 14, 83 (1984).

The starting materials of the formula X can be prepared by reaction of benzyl carbamate ($NH_2$-Z) with the appropriate glyoxylate ester of the formula $R^2O$—C(=O)—CHO, followed by acetylation with acetic anhydride, viz:

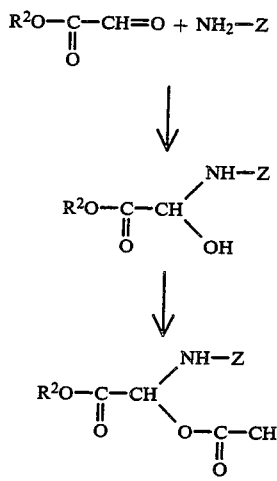

The beta-lactamase inhibitors of this invention of formulae I and II are acidic, and they will form salts with basic agents. All such salts are considered to be within the scope of this invention, although for the purpose of administering a salt of a compound of formula I or II to a mammalian subject, it is necessary to use a pharmaceutically-acceptable (i.e. non-toxic) salt. Moreover, when $R^1$ is alkyl having 1 to 4 carbons, a compound of formula I or II is a mono-acid and will form a mono-salt. However, when $R^1$ is hydrogen, a compound of formula I or II is a diacid and can form disalts. In the latter case, the two cationic counterions can be the same or different.

Salts of the compounds of formulae I and II can be prepared by standard methods for penicillanic acid derivatives. Typically, this involves contacting the acidic and basic components in the appropriate stoichiometric ratio in a inert solvent system. This latter system can be aqueous, non-aqueous or partially aqueous, as appropriate. Salt formation takes place rapidly and then the salt is recovered by filtration, by precipitation with a non-solvent followed by filtration, by evaporation of the solvent, or in the case of aqueous solutions by lyophilization, as appropriate. Basic agents which are suitably employed in salt formation belong to both the organic and inorganic types, and they include ammonia, organic amines, alkali alkoxides, as well as alkaline earth metal hydroxides, carbonates, hydrides and alkoxides. Representative examples of such bases are primary amines such as n-propylamine, n-butylamine, cyclohexylamine, benzylamine and octylamine; secondary amines, such as diethylamine, dicyclohexylamine, morpholine, pyrrolidine and piperidine; tertiary amines, such as triethylamine, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate, and potassium bicarbonate; and alkali metal salts of long-chain fatty acids, such as sodium 2-ethylhexanoate.

Favorable pharmaceutically-acceptable salts of the compounds of formulae I and II are sodium, potassium, calcium, and triethylamine salts.

Also within the scope of this invention are the pharmaceutically-acceptable esters of the compounds of the formula I and II which are readily hydrolyzable in vivo. Such esters are prepared by standard methods for penicillanic acid compounds, with the specific method being chosen being dependent upon precise ester to be prepared. However, when the ester-forming radical is a 3-phthalidyl, 4-crotonolactonyl, or gamma-butyrolacton4-yl radical, or a radical of the formula —CH($R^4$)—O—C(=O)—$R^5$, wherein $R^4$ is hydrogen, methyl or ethyl and $R^5$ is alkyl having 1 to 5 carbons or alkoxy having 1 to 5 carbons, the esters can be prepared by alkylation of a carboxylate salt of a compound of formula I or II with a 3-phthalidyl, 4-crotonolactonyl or gamma-butyrolacton-4-yl halide or a compound of the formula W—CH($R^4$)—O—C(=O)—$R^5$, wherein W is halo and $R^4$ and $R^5$ are as above. In this context, "halide" and "halo" are intended to indicate derivatives of chlorine, bromine and iodine.

Esterification of a compound of formula I or II with a 3-phthalidyl, 4-crotonolactonyl or gamma-butyrolacton-4-yl halide or a halide of the formula W—CH($R^4$)—O—C(=O)—$R^5$ can be carried out by dissolving a carboxylate salt of a compound of formula I or II in a suitable, polar organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover the product by solvent evaporation. Salts of the starting material which are commonly used are alkali metal salts, such as sodium and potassium salts, and tertiary amine salts, such as triethylamine, ethyldiisopropylamine, N-ethylpiperidine, N,N-dimethylaniline and N-methylmorpholine salts. The reaction is run at a temperature in the range from about 0 to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to 24 hours are commonly used.

In regard to esters readily hydrolyzable in vivo of a compound of the formula I or II, it will be appreciated that when $R^1$ is alkyl having 1 to 4 carbons only monoesters can be formed. However, in a compound of formula I or II when $R^1$ is hydrogen, monoesters and diesters readily hydrolyzable in vivo are possible. In the latter case, both the monoesters and the diesters, and mixtures thereof, are within the scope of this invention. Moreover, in diesters readily hydrolyzable in vivo, the two ester-forming radicals can be the same or different.

The compounds of the formula I and II are inhibitors of bacterial beta-lactamases, and they increase the antibacterial effectiveness of beta-lactamase susceptible beta-lactam antibiotics against beta-lactamase producing bacteria in vitro. The manner in which the compounds of formulae I and II increase the effectiveness of a beta-lactam antibiotic in vitro can be appreciated by reference to experiments in which the MIC (Minimum Inhibitory Concentration) of a given antibiotic alone, and said compound of the formula I or II alone, are measured. These MIC's are then compared with the MIC values obtained with a combination of the given antibiotic and the compound of the formula I or II. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society for Microbiology.

The compounds of formulae I and II, and the pharmaceutically-acceptable salts thereof, and the pharmaceutically-acceptable esters thereof readily hydrolyzable in vivo, increase the antibacterial effectiveness of beta-lactamase susceptible beta-lactam antibiotics in vivo. That is, they increase the effectiveness of the antibiotic against infections caused by beta-lactamase-producing microorganisms in mammalian subjects. This makes the compounds of formulae I and II, and said pharmaceutically-acceptable salts and esters thereof, valuable for co-administration with beta-lactam antibiotics in the treatment of bacterial infections in mammalian subjects, particularly humans. In the treatment of a bacterial infection, said compound of the formula I or II or salt or ester thereof can be comingled with the beta-lactam antibiotic, and the two agents thereby administered simultaneously. Alternatively, said compound of the formula I or II or salt or ester thereof can be administered as a separate agent during a course of treatment with a beta-lactam antibiotic. In some instances it will be advantageous to pre-dose the subject with the compound of the formula I or II or salt or ester thereof before initiating treatment with a beta-lactam antibiotic. In general a compound of the formula I or II or salt or ester thereof can be administered orally or parenterally. However, the compounds of formula I and II themselves (i.e. the free acids), and the salts thereof, tend to be more effective when administered parenterally, whereas in many instances formation of an ester readily hydrolyzable in vivo increases oral effectiveness.

When using a compound of formula I or II or pharmaceutically-acceptable salt or ester thereof to enhance the effectiveness of a beta-lactam antibiotic in a human subject, it can be administered alone, or it can be mixed with pharmaceutically-acceptable carriers or diluents. The carrier or diluent is chosen on the basis of the intended mode of administration. For example, when considering the oral mode of administration, a compound of this invention can be used in the form of tablets, capsules, lozenges, troches, powders, syrups, elixirs, aqueous solutions, and suspensions, and the like, in accordance with standard pharmaceutical practice. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral adminstration in capsule form, useful diluents are lactose and high molecular weight polyethylene glycols, e.g. polyethylene glycols having molecular weights from 2,000 to 4,000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic. In a pharmaceutical composition containing a compound of this invention, the weight ratio of active ingredient to carrier will normally be in the range from 1:4 to 4:1.

When using a compound of the formula I or II, or a salt or ester thereof, in combination with a beta-lactamase susceptible beta-lactam antibiotic to treat a mammalian subject suffering from a bacterial infection caused by a beta-lactamase-producing microorganism, the daily dosage to be used will be decided by the prescribing physician or veterinarian. However, in most instances, an effective beta-lactamase inhibiting dose of a compound of the formula I or II, or pharmaceutically-acceptable salt or ester thereof, will be a daily dose in the range from about 10 to about 200 mg per kilogram of body weight orally, and from about 10 to about 400 mg per kilogram of body weight parenterally. Moreover, the weight ratio of the compound of formula I or II, or salt or ester thereof, and the beta-lactam antibiotic with which it is being administered will normally be in in the range from 1:4 to 4:1. However, in some cases, it may be necessary to use dosages and weight ratios outside these ranges.

Typical beta-lactam antibiotics with which a compound of formula I or II, or salt or ester thereof, can be co-administered are:

6-(2-phenylacetamido)penicillanic acid (penicillin G),
6-(2-phenoxyacetamido)penicillanic acid (penicillin V),
6-(D-2-amino-2-phenylacetamido)penicillanic acid (ampicillin),
6-(D-2-amino-2-[4-hydroxyphenyl]acetamido)penicillanic acid (amoxicillin),
6-(2-carboxy-2-phenylacetamido)penicillanic acid (carbenicillin),
1-(ethoxycarbonyloxy)ethyl 6-(D-2-amino-2-phenylacetamido)penicillanate (bacampicillin),
7-(2-[2-thienyl]acetamido)cephalosporanic acid (cephalothin),
7-(2-[1-tetrazolyl]acetamido)-3-([5-methyl-1,3,4-thiadiazol-2-yl]thiomethyl)-3-desacetoxymethylcephalosporanic acid (cefazolin) and
7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxycephalosporanic acid (cefoperazone),
and the pharmaceutically-acceptable salts thereof.

As will be appreciated by one skilled in the art, some of the above beta-lactam antibiotics are effective when administered orally or parenterally, while others are effective only when administered by the parenteral route. When a compound of formula I or II, or a salt or an ester thereof readily hydrolyzable in vivo, is to be used simultaneously (i.e. co-mingled) with a beta-lactam antibiotic which is effective only on parenteral administration, a combination formulation suitable for parenteral use will be required. When the compound of formula I or II or salt or ester thereof is to be used simultaneously (co-mingled) with a beta-lactam antibiotic which is effective orally or parenterally, combinations suitable for either oral or parenteral administration can be prepared. Additionally, it is possible to administer preparations of the compound of formula I or II or salt or ester thereof orally, while at the same time administering a beta-lactam antibiotic parenterally; and it is also possible to admininister preparations of the compound of formula I or II or salt or ester thereof parenterally, while at the same time administering a beta-lactam antibiotic orally.

The following examples and preparation are being provided solely for the purpose of further illustration. Nuclear magnetic resonance spectra ($^1$H) were measured at 60, 250 or 300 MHz, and peak positions are reported in parts per million (ppm) downfield from internal tetramethylsilane. The following abbreviations for peak shapes are used: s, singlet; bs, broad singlet; d, doublet; bd, broad doublet; dd, two doublets; q, quartet; and m, multiplet.

EXAMPLE 1

(8S)-6-beta-[(Hydroxy)(methoxycarbonyl)methyl]-penicillanic Acid 1,1-Dioxide

To a slurry of 0.411 g of prehydrogenated 10% palladium-on-carbon in 15 ml of distilled water was added a solution of 0.411 g of benzyl (8S)-6-beta-[(hydroxy)(methoxycarbonyl)methyl]penicillanate 1,1-dioxide in 15 ml of tetrahydrofuran. The resulting mixture was shaken under an atmosphere of hydrogen at an initial pressure of ca 5 kg/cm$^2$ for 30 minutes, and then it was filtered. The spent catalyst was washed with water and tetrahydrofuran, and the combined washings and filtrate were evaporated in vacuo to remove the tetrahydrofuran. The residual aqueous phase was adjusted to pH 2.2 and extracted with ethyl acetate. The combined extracts were dried (MgSO$_4$) and then concentrated in vacuo to give 0.27 g of the title compound as an oil.

The NMR spectrum (60 MHz; DMSO-d$_6$) showed absorptions at 1.36 (s,3H), 1.46 (s,3H), 3.66 (s,3H), 4.06 (dd,1H,J$_1$=5Hz,J$_2$=11Hz), 4.26 (s,1H), 4.88 (d,1H,J=11Hz) and 5.10 (d,1H,J=5Hz) ppm.

EXAMPLE 2

Sodium Salt of (8S)-6-beta-[(Hydroxy)(methoxycarbonyl)methyl]-penicillanic Acid 1,1-Dioxide The product of Example 1 (0.27 g) was partitioned between 30 ml of ethyl acetate and 20 ml of distilled water, and the pH of the aqueous phase was adjusted to 5.2 with sodium bicarbonate solution. The layers were separated, and the aqueous phase was lyophilized. This afforded 0.27 g of the title sodium salt.

EXAMPLE 3

(8R)-6-beta-[(Hydroxy)(methoxycarbonyl)methyl]-penicillanic Acid 1,1-Dioxide

Hydrogenolysis of 0.4 g of benzyl (8R)-6-beta-[(hydroxy)(methoxycarbonyl)methyl]penicillanate 1,1-dioxide over 10% palladium-on-carbon, using the procedure of Example 1, gave 0.24 g of the title compound.

The NMR spectrum of the product (60 MHz; DMSO-d$_6$) showed absorptions at 1.39 (s,3H), 1.50 (s,3H), 3.69 (s,3H), 4.29 (s,1H), 4.30 (dd,1H,J$_1$=5Hz, J$_2$=11Hz), 4.77 (d,1H,J=11Hz) and 5.09 (d,1H,J=5Hz) ppm.

The above free acid (0.24 g) was converted into 0.2 g of its sodium salt, using the procedure of Example 2.

EXAMPLE 4

(8RS)-6-alpha-[(Hydroxy)(methoxycarbonyl)methyl]-penicillanic Acid 1,1-Dioxide

Hydrogenolyis of 0.36 g of benzyl (parenthesis 8RS)-6-alpha-[(hydroxy)(methoxycarbonyl)methyl]penicillanate 1,1-dioxide over 10% palladium-on-carbon, using the procedure of Example 1, gave 0.23 g of the title compound.

The NMR spectrum of the product (300 MHz; DMSO-d$_6$) showed absorptions at 1.40 (s,3H), 1.51 (s,3H), 3.73 (s,3H) 3.98 (dd,1H,J$_1$=2Hz, J$_2$=5Hz), 4.36 (s,1H), 4.69 (d,1H,J=5Hz), 5.03 (d,1H,J=2Hz) and 6.58 (bs,1H) ppm.

The above free acid (0.23 g) was converted into its sodium salt (0.23 g), using the procedure of Example 2.

EXAMPLE 5

The following carboxylic acids can be prepared by hydrogenolysis of their benzyl esters, using the procedure of Example 1:

(8RS)-6-beta-[(hydroxy)(isopropoxycarbonyl)methyl]-penicillanic acid 1,1-dioxide,
(8RS)-6-beta-[(hydroxy)(butoxycarbonyl)methyl]-penicillanic acid 1,1-dioxide,
(8RS)-6-beta-[(isovaleroyloxy)(methoxycarbonyl)methyl]penicillanic acid 1,1-dioxide,
(8RS)-6-alpha-[(hydroxy)(butoxycarbonyl)methyl]-penicillanic acid 1,1-dioxide and
(8RS)-6-alpha-[(valeroyloxy)(methoxycarbonyl)methyl]penicillanic acid 1,1-dioxide.

EXAMPLE 6

(8RS)-6-beta-[(Hydroxy)(carboxy)methyl]penicillanic acid 1,1-dioxide and (8RS)-6-alpha-[(hydroxy)(carboxy)methyl]penicillanic acid 1,1-dioxide can be prepared by hydrogenolysis of benzyl (8RS)-6-beta-[(hydroxy)(benzyloxycarbonyl)methyl]penicillanate 1,1-dioxide and benzyl (8RS)-6-alpha-[(hydroxy)(benzyloxycarbonyl)methyl]penicillanate 1,1-dioxide, respectively. The reaction can be carried out using the procedure of Example 1, except that after removal of the spent catalyst by filtration the product is isolated simply by evaporation of the tetrahydrofuran in vacuo, followed by lyophilization of the aqueous residue.

EXAMPLE 7

(8R)-6-beta-[(Amino)(methoxycarbonyl)methyl]-penicillanic Acid 1,1-Dioxide

To a slurry of 0.3 g of prehydrogenated 10% palladium-on-carbon in 20 ml of distilled water was added a solution of 0.27 g of benzyl (8R)-6-beta-[(azido)(methoxycarbonyl)methyl]penicillanate 1,1-dioxide in 20 ml of tetrahydrofuran. The resulting mixture was shaken under an atmosphere of hydrogen for 30 minutes at an initial hydrogen pressure of ca 5 kg/cm$^2$. The reaction mixture was then filtered, and the spent catalyst was washed with tetrahydrofuran followed by water. The combined washings and filtrate were concentrated in vacuo to remove the organic solvent and then the residual aqueous phase was extracted with ethyl acetate. The aqueous phase (pH=4.0) was lyophilized to give 0.14 g of the title compound as a white powder.

The NMR spectrum (250 MHz; DMSO-$d_6$) showed absorptions at 1.34 (s,3H), 1.44 (s,3H), 3.66 (s,3H), 4.08 (s,1H), 4.10 (d,1H,J=12Hz), 4.19 (dd,1H,$J_1$=4.5Hz,$J_2$=12Hz) and 5.02 (d,1H,J=4.5Hz) ppm.

EXAMPLE 8

(8S)-6-beta-[(Amino)(methoxycarbonyl)methyl]penicillanic Acid 1,1-Dioxide

To a slurry of 1.2 g of prehydrogenated 10% palladium-on-carbon in 10 ml of distilled water was added a solution of 1.2 g of benzyl (8S)-6-beta-[(benzyloxycarbonylamino)(methoxycarbonyl)methyl]penicillanate 1,1-dioxide in 20 ml of tetrahydrofuran. The resulting mixture was shaken under an at atmosphere of hydrogen at initial hydrogen pressure of ca 5 kg/cm$^2$ for 45 minutes. The reaction mixture was then filtered, and the catalyst was washed with tetrahydrofuran followed by water. The combined washings and filtrate were concentrated in vacuo to remove the organic solvent, and then the residual aqueous phase was extracted with ethyl acetate. The aqueous phase (pH=4.8) was concentrated in vacuo to ca 5 ml and then 10 ml of isopropanol was added. The solid which formed was collected by filtration and dried to give 0.18 g of a first crop of the title compounds as white crystals. The mother liquors from the filtration were concentrated in vacuo to remove the isopropanol, and then the residual aqueous phase was lyophilized to give 0.35 g of a second crop of the title compound.

The NMR spectrum (250 MHz; DMSO-$d_6$) of a sample of the title compound from an analogous preparation showed absorptions at 1.36 (s,3H), 1.46 (s,3H), 3.69 (s,3H), 4.14 (dd,1H,$J_1$=5Hz,$J_2$=12Hz), 4.18 (s,1H), 4.50 (d,1H,J=12Hz) and 5.12 (d,1H,J=5Hz) ppm.

EXAMPLE 9

By hydrogenolysis of the appropriate benzyl 6-[(benzyloxycarbonylamino)(alkoxycarbonyl)methyl]penicillanate 1,1-dioxide, using the procedure of Example 8, the following compounds can be prepared:

(8S)-6-beta-[(amino)(butoxycarbonyl)methyl]penicillanic acid 1,1-dioxide,
(8RS)-6-alpha-[(amino)(methoxycarbonyl)methyl]penicillanic acid 1,1-dioxide and
(8RS)-6-alpha-[(amino)(butoxycarbonyl)methyl]penicillanic acid 1,1-dioxide.

EXAMPLE 10

(8S)-6-[(Amino)(ethoxycarbonyl)methyl]penicillanic Acid 1,1-Dioxide

To a solution of 3.0 g of benzyl (8S)-6-beta-[(benzyloxycarbonylamino)(ethoxycarbonyl)methyl]penicillanate 1,1-dioxide in 50 ml of tetrahydrofuran was added 30 ml of distilled water and 3.0 g of 10% palladium-on-carbon, and the mixture was shaken under an atmosphere of hydrogen at an initial hydrogen pressure of ca 5 kg/cm$^2$ for 30 minutes. The reaction mixture was filtered through celite (a diatomaceous earth) and the filter pad was washed with tetrahydrofuran and distilled water. The combined filtrate and washings were concentrated in vacuo to remove the organic solvent and the residual aqueous phase was extracted with ethyl acetate. The aqueous phase was set aside, and the ethyl acetate layer was dried ($Na_2SO_4$) and evaporated in vacuo. This gave 1.4 g of (8S)-6-beta-[(benzyloxycarbonylamino)(ethoxycarbonyl)methyl]penicillanic acid 1,1-dioxide.

The latter material was dissolved in 20 ml of ethyl acetate, and 20 ml of distilled water and 2.0 g of 10% palladium-on-carbon were added. The resulting mixture was shaken under an atmosphere of hydrogen at an initial hydrogen pressure of ca 5 kg/cm$^2$ for 60 minutes, and then it was filtered. The residue was washed with tetrahydrofuran and water, and the combined filtrate and washings were concentrated in vacuo to remove the organic solvents. The residual aqueous phase was washed with ethyl acetate and the washed aqueous phase was combined with the aqueous phase which had been set aside from the initial hydrogenation. This combined aqueous solution (pH=2.7) was evaporated in vacuo to give 1.2 g of the title compound as a white crystalline solid, containing 0.5 moles of tetrahydrofuran of solvation.

The NMR spectrum (60 MHz; DMSO-$d_6$) showed absorptions at 1.26 (t,3H,J=7 Hz), 1.38 (s,3H), 1.50 (s,3H), 1.79 and 3.57 (m,4H), 4.19 (q,2H, J=7 Hz), 4.30 (s,1H), 4.5–4.9 (m,3H) and 5.26 (d,1H,J=4 Hz) ppm.

EXAMPLE 11

(8S)-6-beta-[(Amino)(carboxy)methyl]penicillanic Acid 1,1-Dioxide, Monosodium Salt Benzyl (8S)-6-beta-[(benzyloxycarbonylamino)(benzyloxycarbonyl)methyl]penicillanate 1,1-dioxide (0.62 g) was hydrogenated over 10% palladium-on-carbon using the procedure of Example 7, except that the pH of the aqueous phase was adjusted to 5.1 with dilute NaOH immediately before lyophilization. This afforded 0.33 g of the title compound.

EXAMPLE 12

(8RS)-6-alpha-[(Amino)(ethoxycarbonyl)methyl]penicillanic Acid 1,1-Dioxide

Benzyl (8RS)-6-alpha-[(benzyloxycarbonylamino)(ethoxycarbonyl)methyl]penicillanate 1,1-dioxide (0.9 g) was hydrogenated over 10% palladium-on-carbon, substantially according to the procedure of Example 8. This afforded 0.45 g of the title compound.

The NMR spectrum of the product (250 MHz; DMSO-$d_6$) showed absorptions at 1.24 (m,3H), 1.37 (bs,3H), 1.49 (s,3H), 3.94 (dd,0.5H,$J_1$=2 Hz,$J_2$=7 Hz), 4.1–4.4 (m,4H), 4.6 (d,0.5H,J=6 Hz), 5.07 (d,1H,J=2 Hz) and 5.33 (d,1H,J=2 Hz) ppm.

EXAMPLE 13

(8RS)-6-alpha-[(Amino)(carboxy)methyl]penicillanic Acid 1,1-Dioxide, Monosodium Salt To a solution of 0.4 g of benzyl (8RS)-6-alpha-[(benzyloxycarbonylamino)(benzyloxycarbonyl)methyl]penicillanate 1,1-dioxide in 20 ml of tetrahydrofuran was added 10 ml water, 0.4 g of 10% palladium-on-carbon and a solution of 54.2 mg of sodium bicarbonate in 5 ml of water. The resulting mixture was hydrogenated according to the procedure of Example 7. This afforded 0.22 g of the title compound.

EXAMPLE 14

Pivaloyloxymethyl
(8R)-6-beta-[(Hydroxy)(methoxycarbonyl)methyl]-
penicillanate 1,1-Dioxide To a stirred solution of 3.05 g (10 mmole) of (8R)-6-beta-[(hydroxy)(methoxycarbonyl)methyl]penicillanic acid 1,1-dioxide in 15 ml of N,N-dimethylformamide is added, at 0° C., 1.42 g (11 mmole) of diisopropylethylamine, followed by 1.35 g (11 mmole) of chloromethyl pivalate and 20 mg of potassium iodide. After 1 hour, the cooling bath is removed, and stirring is continued for 16 hours at ambient temperature. The reaction mixture is diluted with 75 ml of water, and then it is extracted with ethyl acetate. The extracts are washed with water, followed by saturated sodium bicarbonate, and dried using sodium sulfate. Evaporation of the solvent in vacuo then affords the title compound. The title compound can be purified by chromatography on silica gel.

EXAMPLE 15

1-(Ethoxycarbonyloxy)ethyl
(8S)-6-beta-[(Hydroxy)(methoxycarbonyl)methyl]-
penicillanate 1,1-Dioxide The title compound can be prepared by esterification of (8S)-6-beta-[(hydroxy)(methoxycarbonyl)methyl]-penicillanic acid 1,1-dioxide with 1-chloroethyl ethyl carbonate, using the procedure of Example 14.

EXAMPLE 16

Benzyl
(8S)-6-beta-[(Trifluoromethylsulfonyloxy)(methoxycarbonyl)methyl]penicillanate A stirred solution of 0.9 g (2.37 mmole) of benzyl (8S)-6-beta-[(hydroxy)(methoxycarbonyl)methyl]-penicillanate in 20 ml of dichloromethane was cooled to ca −15° C., and 0.211 ml (2.61 mmole) of pyridine, followed by 0.399 ml (2.37 mmole) of trifluoromethanesulfonic anhydride, was added. Stirring was continued at ca −15° C. for 20 minutes, and this afforded the title compound in solution.

An aliquot (1 ml) was removed from the latter solution. The aliquot was washed with water, dried (Na$_2$SO$_4$), and concentrated in vacuo to give a small sample of the title compound. The NMR spectrum of this product (60 MHz; CDCl$_3$) showed absorptions at 1.41 (s,2H), 1.65 (s,3H), 3.82 (s,3H), 3.97 (dd,1H,J$_1$=4 Hz,J$_2$=12 Hz), 4.50 (s,1H), 5.14 (s,2H), 5.47 (d,1H,J=4 Hz), 5.59 (d,1H,J=12 Hz) and 7.3 (s,5H) ppm.

EXAMPLE 17

By esterification of benzyl (8RS)-6-beta-[(hydroxy)(butoxycarbonyl)methyl]penicillanate and benzyl (8RS)-6-beta-[(hydroxy)(benzyloxycarbonyl)methyl]penicillanate with trifluoromethanesulfonic anhydride, using the procedure of Example 16, the following compounds can be prepared:

benzyl (8RS)-6-beta-[(trifluoromethylsulfonyloxy)(butoxycarbonyl)methyl]penicillanate and
benzyl (8RS)-6-beta-[(trifluoromethylsulfonyloxy)(benzyloxycarbonyl)methyl]penicillanate, respectively.

EXAMPLE 18

Reaction of the products of Example 17 with tetra-n-butylammonium azide according to the procedure of Preparation 14, followed by oxidation with 3-chloroperbenzoic acid according to the procedure of Preparation 1, followed by hydrogenolysis according to the procedure of Example 7, affords the following compounds:

(8RS)-6-beta-[(amino)(butoxycarbonyl)methyl]penicillanic acid 1,1-dioxide and
(8RS)-6-beta-[(amino)(carboxy)methyl]penicillanic acid 1,1-dioxide, respectively.

EXAMPLE 19

By esterification of benzyl (8RS)-6-alpha-[(hydroxy)(methoxycarbonyl)methyl]penicillanate, benzyl (8RS)-6-alpha-[(hydroxy)(butoxycarbonyl)methyl]-penicillanate and benzyl 6-alpha-[(hydroxy)(benzyloxycarbonyl)methyl]penicillanate with trifluoromethanesulfonic anhydride, using the procedure of Example 16, the following compounds can be prepared:

benzyl (8RS)-6-alpha-[(trifluoromethylsulfonyloxy)(methoxycarbonyl)methyl]penicillanate,
benzyl (8RS)-6-alpha-[(trifluoromethylsulfonyloxy)(butoxycarbonyl)methyl]penicillanate and
benzyl (8RS)-6-alpha-[(trifluoromethylsulfonyloxy)(benzyloxycarbonyl)methyl]penicillanate, respectively.

EXAMPLE 20

Reaction of the products of Example 19 with tetra-n-butylammonium azide according to the procedure of Preparation 14, followed by oxidation with 3-chloroperbenzoic acid according to the procedure of Preparation 1, followed by hydrogenolysis according to the procedure of Example 7, affords the following compounds:

(8RS)-6-alpha-[(amino)(methoxycarbonyl)methyl]-penicillanic acid 1,1-dioxide,
(8RS)-6-alpha-[(amino)(butoxycarbonyl)methyl]-penicillanic acid 1,1-dioxide and
(8RS)-6-alpha-[(amino)(carboxy)methyl]penicillanic acid 1,1-dioxide, respectively.

PREPARATION 1

Benzyl
(8S)-6-beta-[(Hydroxy)(methoxycarbonyl)methyl]-
penicillanate 1,1-Dioxide A solution of 0.6 g (1.58 mmole) of benzyl (8S)-6-beta-[(hydroxy)(methoxycarbonyl)methyl]penicillanate (Batch 3, Preparation 6) and 0.96 g (4.75 mmole) of 3-chloroperbenzoic acid in 30 ml of ethyl acetate was stored at room temperature for 20 hours. It was then diluted with an additional 30 ml of ethyl acetate and the resulting solution was washed with saturated sodium bisulfite solution followed by saturated sodium bicarbonate solution followed by sodium chloride solution. The washed solution was dried (Na$_2$SO$_4$) and concentrated in vacuo to give 0.64 g of an oil. The oil was purified by chromatography on 80 g of silica gel, eluting with 7:3 chloroform-ethyl acetate, to give 411 mg of the title compound.

The NMR spectrum (60 MHz; CDCl$_3$) showed absorptions at 1.23 (s,3H), 1.50 (s,3H), 3.80 (s,3H), 3.95 (dd,1H,J$_1$=5 Hz,J$_2$=11 Hz), 4.40 (s,1H), 4.62 (d,1H,J=5 Hz), 5.14 (q,2H), 5.22 (d,1H,J=11Hz) and 7.29 (s,5H) ppm.

PREPARATION 2

Benzyl (8R)-6-beta-[(Hydroxy)(methoxycarbonyl)methyl]-penicillanate 1,1-Dioxide The title compound was prepared in 68% yield by oxidation of benzyl (8R)-6-beta-[(hydroxy)(methoxycarbonyl)methyl]penicillanate with 3-chloroperbenzoic acid, using the procedure of Preparation 1.

The NMR spectrum of the product (60 MHz, $CDCl_3$) showed absorptions at 1.25 (s,3H), 1.52 (s,3H), 3.45 (bd,1H,J=6 Hz), 3.79 (s,3H), 4.17 (dd,1H,$J_1$=5 Hz,$J_2$=10 Hz), 4.45 (s,1H), 4.65 (d,1H,J=5 Hz), 4.98 (dd,1H,$J_1$=6 Hz,$J_2$=10 Hz), 5.19 (q,2H) and 7.35 (s,5H) ppm.

PREPARATION 3

The following sulfone (1,1-dioxide) compounds can be prepared by oxidation of the corresponding sulfide with 3-chloroperbenzoic acid, using the procedure of Preparation 1:

benzyl (8RS)-6-beta-[(hydroxy)(isopropoxycarbonyl)methyl]penicillanate 1,1-dioxide,
benzyl (8RS)-6-beta-[(hydroxy)(butoxycarbonyl)methyl]penicillanate 1,1-dioxide,
benzyl (8RS)-6-beta-[(valeroyloxy)(methoxycarbonyl)methyl]penicillanate 1,1-dioxide,
benzyl (8RS)-6-beta-[(isovaleroyloxy)(methoxycarbonyl)methyl]penicillanate 1,1-dioxide and
benzyl (8RS)-6-beta-[(hydroxy)(benzyloxycarbonyl)methyl]penicillanate 1,1-dioxide.

PREPARATION 4

Benzyl (8RS)-6-alpha-[(Hydroxy)(methoxycarbonyl)methyl]-penicillanate 1,1-Dioxide To a stirred solution of 0.56 g (1.36 mmole) of benzyl (8RS)-6-beta-[(hydroxy)(methoxycarbonyl)methyl]penicillanate 1,1-dioxide in 10 ml of dichloromethane was added 0.168 ml (1.36 mmole) of 1,5-diazabicyclo[4.3.0]-non-5-ene (DBN). Stirring was continued for 2 minutes, and then 0.081 ml of glacial acetic acid was added followed by 30 ml of dichloromethane. The resulting solution was washed with sodium bicarbonate solution, followed by water, followed by saturated sodium chloride solution. The resulting solution was dried ($Na_2SO_4$) and concentrated in vacuo to give 0.36 g of the title compound as an oil.

The NMR spectrum (60 MHz, CDCl) showed absorptions at 1.24 (s,3H), 1.51 (s,3H), 3.78 (s,3H), 4.00 (dd,1H,$J_1$=2 Hz,$J_2$=4 Hz), 4.35 (s,1H), 4.55 (d,1H,J=2 Hz), 4.65 (d,1H,J=4 Hz), 5.14 (q,2H), and 7.28 (s,5H) ppm.

PREPARATION 5

The following benzyl 6-alpha-substituted-penicillanate compounds can be prepared by epimerization of the corresponding 6-beta-substituted compounds with DBN, using the procedure of Preparation 4:

benzyl (8RS)-6-alpha-[(hydroxy)(butoxycarbonyl)methyl]penicillanate 1,1-dioxide,
benzyl (8RS)-6-alpha-[(valeroyloxy)(methoxycarbonyl)methyl]penicillanate 1,1-dioxide and
benzyl (8RS)-6-alpha-[(hydroxy)(benzyloxycarbonyl)methyl]penicillanate 1,1-dioxide.

PREPARATION 6

Benzyl 6-beta-[(Hydroxy)(methoxycarbonyl)methyl]penicillanate

A solution of 5.7 g (12.7 mmole) of benzyl 6-bromo-6-[(hydroxy)(methoxycarbonyl)methyl]penicillanate (Batch 3, Part A, Preparation 11) and 10.88 ml (37.4 mmole) of tri-n-butyltin hydride in 100 ml of benzene was heated under reflux with stirring, under nitrogen, for 2 hours. The cooled reaction mixture was evaporated in vacuo, and 100 ml of acetonitrile was added to the residue. The upper (acetonitrile) phase was removed and it was extracted with hexane. The resulting acetonitrile solution was then evaporated in vacuo to give the title compound as an oil.

The above oil was purified by column chromatography on 250 g of silica gel. The column was eluted with 9:1 chloroform-ethyl acetate, taking 20 ml fractions. Groups of fractions were combined and evaporated, giving batches of product as follows:

| Batch No. | Fractions | Weight (g) |
|---|---|---|
| 1 | 50–64 | 1.2 |
| 2 | 65–74 | 0.94 |
| 3 | 75–84 | 1.8 |

Batch No. 1 was essentially pure title compound having the (R)-configuration at the 8-position. Its NMR spectrum (60 MHz; $CDCl_3$) showed absorptions at 1.40 (s,3H), 1.64 (s,3H), 3.48 (d,1H,J=8 Hz), 3.80 (s,3H), 3.88 (dd,1H,$J_1$=4 Hz,$J_2$=8 Hz), 4.44 (s,1H), 4.61 (dd,1H,$J_1$=$J_2$=8 Hz), 5.14 (s,2H), 5.40 (d,1H,J=4 Hz) and 7.33 (s,5H) ppm.

Batch No. 2 was a mixture of the title compound having the (R)-configuration and the title compound having the (S)-configuration at the 8-position.

Batch No. 3 was essentially pure title compound having the (S)-configuration at the 8-position. The NMR spectrum (60 MHz; $CDCl_3$) of equivalent material from an analogous preparation showed absorptions at 1.38 (s,3H), 3.30 (d,1H,J=4 Hz), 3.75 (s,3H), 3.79 (dd,1H, $J_1$=4 Hz, $J_2$=10 Hz), 4.44 (s,1H), 4.69 (dd,1H,$J_1$=4 Hz,$J_2$=10 Hz), 5.12 (s,2H), 5.40 (d,1H,J=4 Hz) and 7.27 (s,5H) ppm.

PREPARATION 7

By reduction of benzyl (8RS)-6-bromo-6-[(hydroxy)(isopropoxycarbonyl)methyl]penicillanate, benzyl (8RS)-bromo-6-[(hydroxy)(butoxycarbonyl)methyl]penicillanate and benzyl (8RS)-6-bromo-[(hydroxy)(benzyloxycarbonyl)methyl]penicillanate with tri-n-butyltin hydride, using the procedure of Preparation 6, the following compounds can be prepared:

benzyl (8RS)-6-beta-[(hydroxy)(isopropoxycarbonyl)methyl]penicillanate,
benzyl (8RS)-6-beta-[(hydroxy)(butoxycarbonyl)methyl]penicillanate and
benzyl (8RS)-6-beta-[(hydroxy)(benzyloxycarbonyl)methyl]penicillanate, respectively.

PREPARATION 8

Benzyl (8S)-6-beta-[(Acetoxy)(methoxycarbonyl)methyl]-penicillanate

A solution of 2.2 g (5.8 mmole) of benzyl (8S)-6-beta-[(hydroxy)(methoxycarbonyl)methyl]penicillanate, 2.34 ml (29 mmole) of pyridine and 1.64 ml (17.4 mmole) of acetic anhydride in 20 ml of tetrahydrofuran was stirred under nitrogen for 1 hour, and then the solvent was removed by evaporation in vacuo. The residue was dissolved in 50 ml of ethyl acetate, and the solution was washed with water, followed by sodium bicarbonate solution, followed by saturated sodium chloride solution. The ethyl acetate solution was then dried ($Na_2SO_4$) and evaporated in vacuo to give 2.45 g of the title compound as an oil.

The NMR spectrum of the product (60 MHz; $CDCl_3$) showed absorptions at 1.38 (s,3H), 1.62 (s,3H), 2.15 (s,3H), 3.69 (s,3H), 3.94 (dd,1H,$J_1$=4 Hz,$J_2$=10 Hz), 4.43 (s,1H), 5.13 (s,2H), 5.47 (d,1H,J=4 Hz), 5.78 (d,1H,J=10 Hz) and 7.26 (s,5H) ppm.

PREPARATION 9

Benzyl (8R)-6-beta-[(Acetoxy)(methoxycarbonyl)methyl]penicillanate

The title compound was prepared in essentially quantitative yield by acetylation of benzyl (8R)-6-beta-[(hydroxy)(methoxycarbonyl)methyl]penicillanate, using the procedure of Preparation 8.

The NMR spectrum (60 MHz; $CDCl_3$) of the product showed absorptions at 1.41 (s,3H), 1.67 (s,3H), 2.11 (s,3H), 3.79 (s,3H), 4.01 (dd,1H,$J_1$=4 Hz,$J_2$=11 Hz), 4.48 (s,1H), 5.18 (s,2H), 5.37 (d,1H, J=11 Hz), 5.46 (d,1H,J=4 Hz) and 7.33 (s,5H) ppm.

PREPARATION 10

Benzyl (8RS)-6-beta-[(valeroyloxy)(methoxycarbonyl)methyl]penicillanate and benzyl (8RS)-6-beta-[(isovaleroyloxy)(methoxycarbonyl)methyl]penicillanate can be prepared from benzyl (8RS)-6-beta-[(hydroxy)(methoxycarbonyl)methyl]penicillanate by acylation with valeric anhydride and isovaleric anhydride, respectively, using the procedure of Preparation 8.

PREPARATION 11

Benzyl 6-Bromo-6-[(hydroxy)(methoxycarbonyl)methyl]-penicillanate

Part A

The following three solutions were prepared:

Solution A: 18.9 ml (56.8 mmole) of a 3.0 molar solution of methylmagnesium bromide in diethyl ether was added to 200 ml of dry tetrahydrofuran which had been precooled to ca −78° C., and the resulting mixture was then cooled to ca −78° C.

Solution B: 25.5 g (56.8 mmole) of benzyl 6,6-dibromopenicillanate was dissolved in 75 ml of dry tetrahydrofuran and the solution was cooled to ca −78° C.

Solution C: 7.5 g (82 mmole) of methyl glyoxylate was dissolved in 25 ml of dry tetrahydrofuran and the solution was cooled to ca −78° C.

Solution B was added with stirring through a polytetrafluoroethylene tube, under a partial vacuum, during a 20 second period, to Solution A. Stirring was continued for an additional 100 seconds and then Solution C was added all in one portion with stirring. Stirring was continued for 7 minutes, and then 6.8 ml of glacial acetic acid was added with stirring. The resulting mixture was evaporated in vacuo and the residue was partitioned between ethyl acetate and water. The organic layer was removed, washed with water followed by saturated sodium chloride, dried ($Na_2SO_4$), and evaporated in vacuo. This afforded the title compound as a mixture of diastereomers.

The above mixture of diastereomers was purified by column chromatography on 1 kg of silica gel. The column was eluted initially with 2 liters of chloroform, which was then discarded, and then with 9:1 chloroform-methyl acetate taking 20 ml fractions. Groups of fractions were combined and evaporated in vacuo, giving five batches of product as follows:

| Batch No. | Fractions | Weight (g) | Appearance |
| --- | --- | --- | --- |
| 1 | 40-100 | 13 | — |
| 2 | 101-130 | 3.2 | tan crystals |
| 3 | 131-150 | 6.0 | oil |
| 4 | 151-180 | 3.5 | oil |
| 5 | 181-220 | 1.8 | oil |

Batch No. 1 was a byproduct, which was discarded.

Batch No. 2 was slurried under diisopropyl ether, and recovered by filtration, to give 1.64 g of the title compound as a solid which was largely a single diastereomer (Diastereomer A).

Batches Nos. 3 to 5 were each the title compound as a mixture of two diastereomers (Diastereomer A and Diastereomer B).

Part B

Benzyl 6,6-dibromopenicillanate (44.9 g) was reacted with methylmagnesium bromide (33.3 ml of a 3.0 molar solution in diethyl ether), followed by methyl glyoxylate (8.8 g), and the crude product was purified by chromatography on silica gel, using the procedure of Part A, above. The following batches of product were obtained:

| Batch No. | Fractions | Weight (g) |
| --- | --- | --- |
| 1 | 64-86 | 27 |
| 2 | 113-133 | 6.3 |
| 3 | 134-160 | 6.3 |
| 4 | 161-210 | 3.5 |

Batch No. 1 was discarded.

Batch No. 2 was slurried under 30 ml of diisopropyl ether, and recovered by filtration, to give 4.5 g of the title compound as a single diastereomer (Diastereomer A).

Batch No. 3 was the title compound as a mixture of diastereomers (Diastereomer A and Diastereomer B).

Batch No. 4 was the title compound as a single diastereomer (Diastereomer B).

The NMR spectrum of Diastereomer A (60 MHz; $CDCl_3$) showed absorptions at 1.39 (s,3H), 1.64 (s,3H), 3.63 (d,1H,J=6 Hz), 3.88 (s,3H), 4.57 (s,1H), 4.69 (d,1H,J=6 Hz), 5.18 (s,2H), 5.58 (s,1H) and 7.36 (s,5H) ppm.

The NMR spectrum of Diastereomer B (60 MHz; $CDCl_3$) showed absorptions at 1.40 (s,3H), 1.63 (s,3H), 3.70 (bs,1H), 3.80 (s,3H), 4.52 (s,1H), 4.69 (d,1H,J=6 Hz), 5.17 (s,2H), 5.59 (s,1H) and 7.36 (s,5H) ppm.

PREPARATION 12

The following compounds can be prepared by reaction of benzyl 6,6-dibromopenicillanate with methylmagnesium bromide, followed by the appropriate ester of glyoxylic acid, according to the procedure of Preparation 11:

benzyl 6-bromo-6-[(hydroxy)(isopropoxycarbonyl)methyl]penicillanate, benzyl 6-bromo-6-[(hydroxy)(butoxycarbonyl)methyl]penicillanate and benzyl 6-bromo-6-[(hydroxy)(benzyloxycarbonyl)methyl]penicillanate.

PREPARATION 13

Benzyl (8R)-6-beta-[(Azido)(methoxycarbonyl)methyl]penicillanate 1,1-Dioxide Oxidation of 0.5 g of benzyl (8R)-6-beta-[(azido)(methoxycarbonyl)methyl]penicillanate with 3-chloroperbenzoic acid, using the procedure of Preparation 1, afforded, after chromatography, 0.31 g of the title compound as an oil.

The NMR spectrum (60 MHz; CDCl$_3$) showed absorptions at 1.28 (s,3H), 1.55 (s,3H), 3.84 (s,3H), 4.25 (dd,1H,J$_1$=5 Hz,J$_2$11Hz), 4.42 (s,1H), 4.60 (d,1H,J=5 Hz), 4.91 (d,1H,J=11 Hz), 5.16 (q,2H) and 7.29 (s,5H) ppm.

PREPARATION 14

Benzyl (8R)-6-beta-[(Azido)(methoxycarbonyl)methyl]penicillanate

To the solution of benzyl (8S)-6-beta-[(trifluoromethylsulfonyloxy)(methoxycarbonyl)methyl]penicillanate from Example 16 was added 0.677 g of tetra-n-butylammonium azide at ca $-15°$ C., with stirring. Stirring was continued at ca $-15°$ C. for 2 hours, and then a further 0.677 g of tetra-n-butylammonium azide was added. The resulting mixture was stored at ca 5° C. overnight and then it was passed through a chromatography column containing 25 g of silica gel. The eluate was discarded, and the column was eluted further with 9:1 chloroform-ethyl acetate, taking 50 ml fractions. The appropriate fractions were combined and concentrated in vacuo to give 0.5 g of the title compound.

The NMR spectrum (60 MHz; CDCl$_3$) showed absorptions at 1.43 (s,3H), 1.64 (s,3H), 3.88 (s,3H), 3.95 (dd,1H,J$_1$=4 Hz,J$_2$=11 Hz), 4.39 (d,1H,J=11 Hz), 4.45 (s,1H), 5.18 (s,2H), 5.44 (d,1H,J=4 Hz) and 7.37 (s,5H) ppm.

PREPARATION 15

Benzyl (8S)-6-beta-[(Benzyloxycarbonylamino)(methoxycarbonyl)methyl]penicillanate 1,1-Dioxide Oxidation of 5.9 g (11.5 mmole) of benzyl (8S)-6-beta-[(benzyloxycarbonylamino)(methoxycarbonyl)methyl]penicillanate with 6.98 g (34.5 mmole) of 3-chloroperbenzoic acid, substantially according to the procedure of Preparation 1, gave 4.7 g of the title compound, after chromatography.

The NMR spectrum (250 MHz; DMSO-d$_6$) showed absorptions at 1.29 (s,3H), 1.46 (s,3H), 3.69 (s,3H), 4.30 (dd,1H,J$_1$=4 Hz,J$_2$=12 Hz), 4.64 (s,1H), 5.10 (q,2H), 5.14 (dd,1H,J$_1$=9 Hz,J$_2$=12 Hz), 5.28 (q,2H), 5.34 (d,1H,J=4 Hz), 7.33–7.48 (m,10H) and 7.99 (d,1H,J=9 Hz) ppm.

PREPARATION 16

Benzyl (8S)-6-beta-[(Benzyloxycarbonylamino)(ethoxycarbonyl)methyl]penicillanate 1,1-Dioxide Oxidation of 5.0 g (9.5 mmole) of benzyl (8S)-6-beta-[(benzyloxycarbonylamino)(ethoxycarbonyl)methyl]penicillanate with 5.76 g (28.5 mmole) of 3-chloroperbenzoic acid, substantially according to the procedure of Preparation 1 gave 5.0 g of the title compound, which was not chromatographed.

The NMR spectrum of the product (60 MHz; CDCl$_3$) showed absorptions at 1.22 (t,3H,J=7 Hz), 1.24 (s,3H), 1.49 (s,3H), 4.15 (q,2H,J=7 Hz), 4.39 (s,1H), 4.1–4.5 (m,1H), 4.70 (d,1H,J=4 Hz), 5.03 (s,2H), 5.13 (q,2H), 4.92–5.2 (m,1H), 5.70 (d,1H,J=8 Hz), 7.22 (s,5H) and 7.28 (s,5H) ppm.

PREPARATION 17

Benzyl (8S)-6-beta-[(Benzyloxycarbonylamino)(benzyloxycarbonyl)methyl]penicillanate 1,1-Dioxide Oxidation of 1.8 g (3.06 mmole) of benzyl (8S)-6-beta-[(benzyloxycarbonylamino)(benzyloxycarbonyl)methyl]penicillanate with 1.8 g (9.18 mmole) of 3-chloroperbenzoic acid, substantially according to the procedure of Preparation 1, gave 1.4 g of the title compound, after chromatography.

The NMR spectrum (60 MHz; CDCl$_3$) of the product showed absorptions at 1.22 (s,3H), 1.50 (s,3H), 4.40 (s,1H), 4.66 (d,1H,J=5 Hz), 4.3–4.8 (m,1H), (m,7H), 5.51 (bd,1H,J=8 Hz) and 7.2–7.3 (m,15H) ppm.

PREPARATION 18

Benzyl (8S)-6-beta-[(Benzyloxycarbonylamino)(methoxycarbonyl)methyl]penicillanate A mixture of 2.8 g (4.9 mmole) of benzyl 6-bromo-6-[(benzyloxycarbonylamino)(methoxycarbonyl)methyl]penicillanate, 4.3 ml (14.75 mmole) of tri-n-butyltin hydride and 70 ml of benzene was stirred at room temperature for 24 hours. The solvent was removed by evaporation in vacuo, and the residue was washed several times with hexane and then dried under high vacuum. The product thus obtained was chromatographed on 400 g of silica gel, eluting with 19:1 chloroform-ethyl acetate. The appropriate fractions were combined and evaporated in vacuo to give 1.5 g of the title compound as a viscous oil.

The NMR spectrum (60 MHz; CDCl$_3$) showed absorptions at 1.38 (s,3H), 1.60 (s,3H), 3.70 (s,3H), 3.90 (dd,1H,J$_1$=4 Hz,J$_2$=11 Hz), 4.43 (s,1H), 4.81 (dd,1H,J$_1$=8 Hz,J$_2$=11 Hz), 5.10 (s,2H), 5.15 (s,2H), 5.48 (d,1H,J=4 Hz), 5.56 (bd,1H,J=8 Hz), 7.27 (s,5H) and 7.32 (s,5H) ppm.

PREPARATION 19

Benzyl (8S)-6-beta-[(Benzyloxycarbonylamino)(ethoxycarbonyl)methyl]penicillanate Benzyl 6-bromo-6-[(benzyloxycarbonylamino)(ethoxycarbonyl)methyl]penicillanate (14.0 g, 23.1 mmole) was reduced with 18.2 ml (69.4 mmole) of tri-n-butyltin hydride in 100 ml of benzene, according to the procedure of Preparation 18, except that the reaction mixture was heated under reflux for 3 hours instead of being stirred for 24 hours at room temperature. After chromatography, there was obtained 7.1 g of the title compound.

The NMR spectrum (60 MHz, CDCl$_3$) of the product showed absorptions at 1.22 (t,3H,J=7 Hz), 1.39 (s,3H), 1.62 (s,3H), 3.90 (dd,1H,J$_1$=4 Hz,J$_2$=11 Hz), 4.13 (q,2H,J=7 Hz), 4.45 (s,1H), 4.81 (dd,1H,J$_1$=8 Hz,J$_2$=11 Hz), 5.09 (s,2H), 5.14 (s,2H), 5.46 (d,1H,J=4 Hz), 5.53 (d,1H,J=8 Hz) and 7.3 (m,10H) ppm.

PREPARATION 20

Benzyl (8S)-6-beta-[(Benzyloxycarbonylamino)(benzyloxycarbonyl)methyl]penicillanate Benzyl 6-bromo-6-[(benzyloxycarbonylamino)(benzyloxycarbonyl)methyl]penicillanate (6.8 g, 10.2 mmole) was reduced with 8.9 ml (30.6 mmole) of tri-n-butyltin hydride in 100 ml of benzene, using the procedure of Preparation 18, except that the reaction was refluxed for 2.5 hours. After chromatography, there was obtained 2.3 g of the title compound.

The NMR spectrum (60 MHz, CDCl$_3$) of the product showed absorptions at 1.32 (s,3H), 1.55 (bs,3H), 3.86 (dd,1H,J$_1$=4 Hz,J$_2$=11 Hz), 4.40 (s,1H), 4.85 (dd,1H,J$_1$=8 Hz,J$_2$=11 Hz), 5.0–5.1 (m,6H), 5.36 (d,1H,J=4 Hz), 5.72 (d,1H,J=8 Hz) and 7.1–7.3 (m,15H) ppm.

PREPARATION 21

Benzyl 6-Bromo-6-[(benzyloxycarbonylamino)(methoxycarbonyl)methyl]penicillanate Benzyl 6,6-dibromopenicillanate (28.6 g, 63.6 mmole) was reacted with methylmagnesium bromide (38.2 ml of a 3.0 molar solution in diethyl ether, 114 mmole), followed by methyl 2-(benzyloxycarbonylamino)-2-(acetoxy)acetate (17.8 g, 63.6 mmole), and the crude product was purified by chromatography on silica gel, using the procedure of Part A of Preparation 11. The following batches of product were obtained:

| Batch No. | Fractions | Weight (g) |
|---|---|---|
| 1 | 18–30 | 6.5 |
| 2 | 31–50 | 10.2 |
| 3 | 51–80 | 5.5 |
| 4 | 81–120 | 6.5 |
| 5 | 121–160 | 2.3 |

Batch No. 1 was a byproduct which was discarded.
Batch No. 2 was the title compound together with some byproduct.
Batch No. 3 was the title compound.
Batch No. 4 was the title compounds together with some ester starting material.
Batch No. 5 was a byproduct which was discarded.
Batch No. 2 was rechromatographed on 400 g of silica gel, eluting with 9:1 chloroform-hexane. The appropriate fractions were combined and evaporated in vacuo to give 4.2 g of the title compound, largely as a single diastereomer. The NMR spectrum (60 MHz; CDCl$_3$) of the major component showed absorptions at 1.36 (s,3H), 1.59 (s,3H), 3.75 (s,3H), 4.46 (s,1H), 4.99 (d,1H,J=10 Hz), 5.07 (s,2H), 5.12 (s,2H), 5.52 (s,1H), 5.59 (bd,1H,J=10 Hz) and 7.25 (s,10H) ppm.

PREPARATION 22

Benzyl 6-Bromo-6-[(benzyloxycarbonylamino)(ethoxycarbonyl)methyl]penicillanate The title compound was prepared in a manner similar to Preparation 21, but replacing the methyl 2-(benzyloxycarbonylamino)-2-(acetoxy)acetate used therein by the corresponding ethyl ester. The NMR spectrum of the major component of the product (60 MHz; CDCl$_3$) showed absorptions at 1.26 (t,3H,J=7 Hz), 1.34 (s,3H), 1.59 (s,3H), 4.20 (q,2H,J=7 Hz), 4.49 (s,1H), 5.02 (d,1H,J=9 Hz), 5.09 (s,2H), 5.13 (s,2H), 5.57 (s,1H), 5.65 (d,1H,J=9 Hz) and 7.3 (m,10H) ppm.

PREPARATION 23

Benzyl 6-Bromo-6-[(benzyloxycarbonylamino)(benzyloxycarbonyl)methyl]penicillanate The title compound was prepared in a manner similar to Preparation 21, but replacing the methyl 2-(benzyloxycarbonylamino)-2-(acetoxy)acetate used therein by the corresponding benzyl ester. The NMR spectrum of the major component of the product (60 MHz; CDCl$_3$) showed absorptions at 1.36 (s,3H), 1.58 (s,3H), 4.48 (s,1H), 4.9–5.3 (m,7H), 5.53 (s,1H), 5.59 (bd,1H,J=10 Hz), 7.2–7.3 (m,15H) ppm.

PREPARATION 24

Benzyl (8RS)-6-alpha-[(Benzyloxycarbonylamino)(ethoxycarbonyl)methyl]penicillanate 1,1-Dioxide Benzyl (8RS)-6-beta-[(benzyloxycarbonylamino)(ethoxycarbonyl)methyl]penicillanate 1,1-dioxide (2.0 g) was epimerized with one molar equivalent of DBN, substantially according to the procedure of Preparation 4 to give 1.4 g of the title compound. The product was purified by chromatography on silica gel, eluting with chloroformethyl-ethyl acetate (9:1). Yield: 0.9 g.

The NMR spectrum of the product (60 MHz; CDCl$_3$) showed absorptions at 1.22 (s,3H), 1.24 (t,3H,J=7 Hz), 1.51 (s,3H), 4.20 (q,2H,J=7 Hz), 3.9–4.3 (m,1H), 4.34 (s,1H), 4.58 (d,0.5H,J=2 Hz), 4.72 (dd,1H,J$_1$=2 Hz,J$_2$=8 Hz), 4.90 (d,0.5H,J=2 Hz), 5.10 (s,2H), 5.14 (m,2H), 5.71 (d,1H,J=8 Hz) and 7.2–7.3 (m,10H) ppm.

PREPARATION 25

Benzyl (8RS)-6-alpha-[(Benzyloxycarbonylamino)(benzyloxycarbonyl)methyl]penicillanate 1,1-Dioxide The title compound was prepared in 65% yield after chromatography by epimerization of the corresponding 6-beta compound with DBN, using the procedure of Preparation 4.

The NMR spectrum of the product (60 MHz, CDCl$_3$) showed absorptions at 1.19 (s,3H), 1.47 (s,3H), 4.05 (m,1H), 4.17 (s,1H), 4.8–5.4 (m,8H), 5.80 (d,0.5H,J=8 Hz), 5.83 (d,0.5H,J=8 Hz) and 7.2–7.3 (m,15H) ppm.

PREPARATION 26

The following benzyl 6-alpha-substituted penicillanate compounds can be prepared by epimerization of the corresponding 6-beta-substituted compound with DBN, using the procedure of Preparation 4 but with an increase in reaction time to about 1 hour:

benzyl (8RS)-6-alpha-[(hydroxy)(methoxycarbonyl)methyl]penicillanate,
benzyl (8RS)-6-alpha-[(hydroxy)(butoxycarbonyl)methyl]penicillanate and
benzyl (8RS)-6-alpha-[(hydroxy)(benzyloxycarbonyl)methyl]penicillanate.

PREPARATION 27

Ethyl 2-(Benzyloxycarbonylamino)-2-(acetoxy)acetate

A solution of 17.3 g (0.169 mole) of ethyl glyoxylate and 23.0 g (0.152 mole) of benzyl carbamate in 250 ml of toluene was heated under reflux for 6 hours, with removal of water using a Dean-Stark trap. The resulting reaction mixture was concentrated in vacuo, and diethyl ether was added to the residue. The mixture was filtered, and the diethyl ether solution was evaporated in vacuo to give 25.0 g of ethyl 2-(benzyloxycarbonylamino)-2-(hydroxy)acetate as a sticky solid.

The above ethyl 2-(benzyloxycarbonylamino)-2-(hydroxy)acetate (24.9 g), 34.2 ml of pyridine and 24.3 ml of acetic anhydride in 250 ml of tetrahydrofuran was stirred at room temperature for 30 minutes. It was then concentrated in vacuo, and dried under high vacuum for 4 hours to give 25.0 g of the title compound.

In like manner, starting with the appropriate glyoxylate ester, the following compounds can be prepared:
methyl 2-(benzyloxycarbonylamino)-2-(acetoxy)acetate and
benzyl 2-(benzyloxycarbonylamino)-2-(acetoxy)acetate.

I claim:

1. A penicillanic acid 1,1-dioxide compound selected from the group consisting of

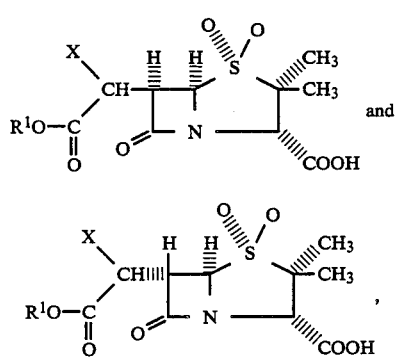

and the pharamaceutically-acceptable base salts thereof, and the pharmaceutically-acceptable esters thereof readily hydrolyzable in vivo, wherein
$R^1$ is selected from the group consisting of hydrogen and alkyl having 1 to 4 carbons;
X is selected from the group consisting of hydroxy, alkanoyloxy having 2 to 5 carbon atoms and amino;
and said pharmaceutically-acceptable esters thereof readily hydrolyzable in vivo are formed from an ester-forming radical selected from the group consisting of 3-phthalidyl, 4-crotonolactonyl, gamma-butyrolacton-4-yl and —$CH(R^4)$—O—C(=O)—$R^5$, wherein $R^4$ is hydrogen, methyl or ethyl and $R^5$ is alkyl of 1 to 5 carbons or alkoxy of 1 to 5 carbons.

2. A compound according to claim 1 of the formula

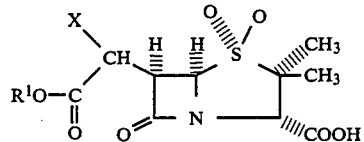

and said pharmaceutically-acceptable base salts thereof, and the pharmaceutically-acceptable esters thereof readily hydrolyzable in vivo.

3. A compound according to claim 2, wherein $R^1$ is said alkyl.

4. A compound according to claim 3, wherein X is hydroxy.

5. A compound according to claim 4, wherein $R^1$ is methyl.

6. A compound according to claim 3, wherein X is amino.

7. A compound according to claim 6, wherein $R^1$ is methyl.

8. A compound according to claim 1 of the formula

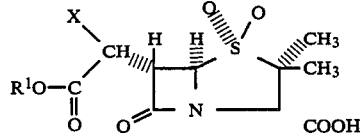

and said pharmaceutically-acceptable base salts thereof, and the pharmaceutically-acceptable esters thereof readily hydrolyzable in vivo.

9. A compound according to claim 8, wherein $R^1$ is said alkyl.

10. A compound according to claim 9, wherein X is amino.

11. A compound according to claim 10, wherein $R^1$ is ethyl.

12. In a method of treating a bacterial infection caused by a beta-lactamase producing microorganism in a mammalian subject with a beta-lactam antibiotic selected from the group consisting of penicillin G, penicillin V, ampicillin, amoxicillin, carbenicillin, bacampicillin, cephalothin, cefazolin and cefoperazone, and the pharmaceutically-acceptable salt thereof, the improvement which comprises:
co-administering with said beta-lactam antibiotic to said mammalian subject an effective beta-lactamase inhibiting amount of a penicillanic acid 1,1-dioxide compound selected from the group consisting of

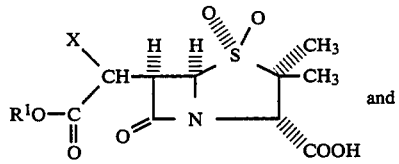

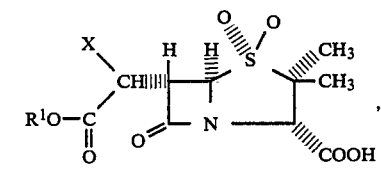

and the pharmaceutically-acceptable base salts thereof, and the pharmaceutically-acceptable esters thereof readily hydrolyzable in vivo, wherein R[1] is selected from the group consisting of hydrogen and alkyl having 1 to 4 carbons;

X is selected from the group consisting of hydroxy, alkanoyloxy having 2 to 5 carbon atoms and amino;

and said pharmaceutically-acceptable esters thereof readily hydrolyzable in vivo are formed from an ester-forming radical selected from the group consisting of 3-phthalidyl, 4-crotonolactonyl, gamma-butyrolacton-4-yl and —CH(R[4])—O—C(=O)—R[5], wherein R[4] is hydrogen, methyl or ethyl and R[5] is alkyl of 1 to 5 carbons or alkoxy of 1 to 5 carbons.

13. The method according to claim 12, wherein said penicillanic acid 1,1-dioxide compound is of the formula

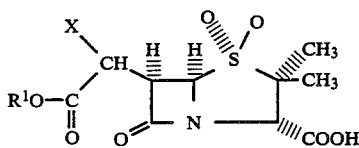

or pharmaceutically-acceptable base salt thereof, or one of said pharmaceutically-acceptable esters thereof readily hydrolyzable in vivo.

14. The method according to claim 13, wherein R[1] is said alkyl.

15. The method according to claim 14, wherein X is hydroxy.

16. The method according to claim 15, wherein R[1] is methyl.

17. The method according to claim 14, wherein X is amino.

18. The method according to claim 17, wherein R[1] is methyl.

19. The method according to claim 12, wherein said penicillanic acid 1,1-dioxide compound is of the formula

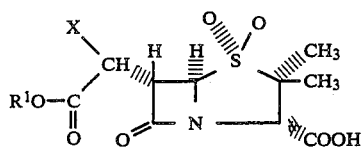

or a pharmaceutically-acceptable base salt thereof, or one of said pharmaceutically-acceptable esters thereof readily hydrolyzable in vivo.

20. The method according to claim 19, wherein R[1] is said alkyl.

21. The method according to claim 20, wherein X is amino.

22. The method according to claim 21, wherein R[1] is ethyl.

23. A pharmaceutical composition, which comprises a penicillanic acid 1,1-dioxide compound according to claim 1 and a pharmaceutically-acceptable carrier, wherein the weight ratio of the penicillanic acid 1,1-dioxide compound to the pharmaceutically-acceptable carrier is in the range from 1:4 to 4:1.

* * * * *